(12) United States Patent
Villavicencio

(10) Patent No.: US 11,691,019 B2
(45) Date of Patent: Jul. 4, 2023

(54) QUADRIPOLAR HEADER CONNECTOR SUPPORT FOR PRE-MOLDED HEADER OF IMPLANTABLE PULSE GENERATOR

(71) Applicant: PACESETTER, INC., Sylmar, CA (US)

(72) Inventor: Brett C. Villavicencio, Valencia, CA (US)

(73) Assignee: Pacesetter, Inc., Sylmar, CA (US)

( * ) Notice: Subject to any disclaimer, the term of this patent is extended or adjusted under 35 U.S.C. 154(b) by 594 days.

(21) Appl. No.: 16/384,500

(22) Filed: Apr. 15, 2019

(65) Prior Publication Data

US 2020/0324122 A1    Oct. 15, 2020

(51) Int. Cl.
| | | |
|---|---|---|
| *A61N 1/375* | (2006.01) | |
| *A61N 1/05* | (2006.01) | |
| *H01B 17/30* | (2006.01) | |
| *A61N 1/08* | (2006.01) | |
| *A61N 1/372* | (2006.01) | |

(52) U.S. Cl.
CPC ....... *A61N 1/3752* (2013.01); *A61N 1/37512* (2017.08); *A61N 1/05* (2013.01); *A61N 1/08* (2013.01); *A61N 1/37229* (2013.01); *A61N 1/37518* (2017.08); *H01B 17/30* (2013.01)

(58) Field of Classification Search
CPC .............. A61N 1/3752; A61N 1/37512; A61N 1/37518; A61N 1/05; A61N 1/08; A61N 1/37229
See application file for complete search history.

(56) References Cited

U.S. PATENT DOCUMENTS

| | | | |
|---|---|---|---|
| 7,309,262 B2 | 12/2007 | Zart et al. | |
| 8,565,884 B2 | 10/2013 | Sherva et al. | |
| 8,673,194 B2 | 3/2014 | Lee et al. | |
| 9,387,335 B2 | 7/2016 | Kane et al. | |
| 9,855,413 B2 | 1/2018 | Vadlamudi et al. | |
| 2008/0139053 A1* | 6/2008 | Ries ................ | A61N 1/3752 439/736 |
| 2013/0012046 A1* | 1/2013 | Jullien ............. | H01R 13/514 439/283 |
| 2013/0309889 A1* | 11/2013 | Ries ................ | H01R 43/24 29/857 |
| 2015/0018877 A1* | 1/2015 | Nolan .............. | B29C 45/14467 606/232 |
| 2015/0306402 A1* | 10/2015 | Ries ................ | A61N 1/3754 439/271 |
| 2017/0056675 A1* | 3/2017 | Bortolin .......... | A61B 5/686 |
| 2017/0354825 A1* | 12/2017 | Dadashian ....... | H01R 13/5219 |
| 2018/0169418 A1* | 6/2018 | Sheldon ........... | H01R 13/639 |

* cited by examiner

*Primary Examiner* — Lynsey C Eiseman
*Assistant Examiner* — Amanda L Steinberg
(74) *Attorney, Agent, or Firm* — The Small Patent Law Group LLC; Dean D. Small

(57) ABSTRACT

Disclosed herein is an implantable pulse generator for administering electrotherapy via an implantable lead. The pulse generator includes a housing and a header connector assembly coupled to the housing. The header connector assembly includes a connector assembly and a header enclosing the connector assembly. The connector assembly includes a support and a connector receptacle. The support extends at least partially about the connector receptacle and is at least partially responsible for having prevented injection molding material from entering the connector receptacle when the injection molding material was injection molded about the connector assembly in forming the header.

11 Claims, 11 Drawing Sheets

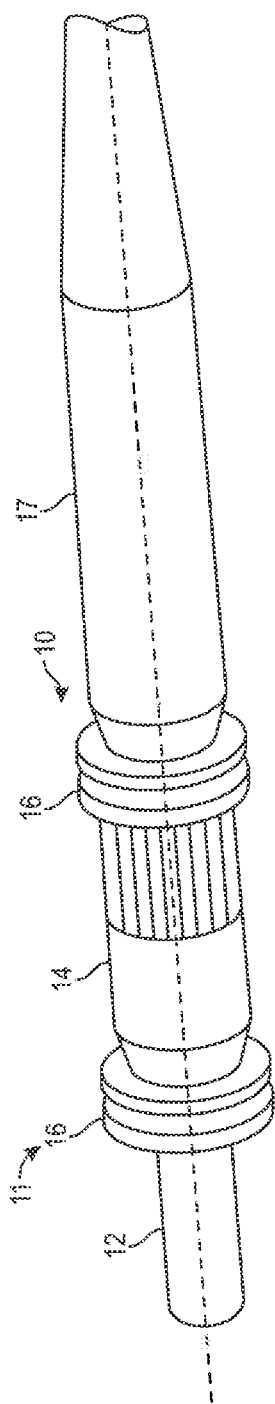
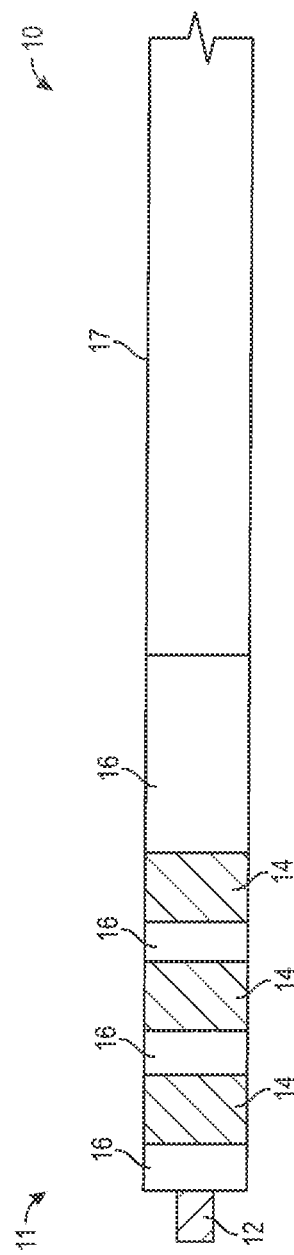
FIG. 1A (Prior Art)
FIG. 1B (Prior Art)

QUADRIPOLAR HEADER CONNECTOR SUPPORT FOR PRE-MOLDED HEADER OF IMPLANTABLE PULSE GENERATOR

FIELD OF THE INVENTION

Aspects of the present invention relate to medical apparatus and methods. More specifically, the present invention relates to an improved pre-molded header connector assembly of an implantable pulse generator and related methods of manufacture.

BACKGROUND OF THE INVENTION

Implantable pulse generators (IPGs) such as pacemakers and implantable cardioverter defibrillators (ICDs), which are used in the treatment of cardiac conditions, and neuromodulators or neurostimulators, which are used in chronic pain management or the actuation and control of other body systems, commonly include a housing, feedthrus, and a connector assembly that is enclosed in a header. Electrical stimulation originating in the housing is led to the connector assembly through feedthrus. The connector assembly serves to transmit electrical signals out of the FIG. and to a lead electrically connected to the connector assembly, the lead transmitting electrical signals between the FIG. and patient tissue.

Current header casting manufacturing processes and the associated methods of assembling the header and its enclosed connector assembly onto the housing require multiple operations, are skill intensive, and unavoidably time consuming. Connector assemblies are first cast into a header separate from the housing, the header and the connector assembly enclosed therein forming a header connector assembly. The header connector assembly is joined with the housing by injecting a thermosetting polymer (e.g., an epoxy) into an interface between the header connector assembly and the housing, such an injection process being called a backfill process. This backfill process creates attachment and electrical sealing between the header connector assembly and the housing, However, the backfill process nearly mirrors the extensive casting process used to encase the connector assembly in the header to form the header connector assembly, the backfill process involving mold set-up, mold pre-heat, epoxy dispense, epoxy curing, and mold breakdown. The backfill process is not only lengthy, but also expensive due to its many tools and equipment, and necessity for many skilled operators.

Due to the low viscosity characteristics of epoxy used in the backfill process, the epoxy has a tendency to flow into undesired areas. A common cause for rework on IPGs involves epoxy entering one or more of the lead connector receiving bores of the header connector assembly, thereby forming a barrier to the establishment of critical electrical connections between the electrical terminals of the lead connector ends and the electrical contacts of the connector assembly, Such FIG. rework further extends costs and manufacturing times. Other causes for rework are experienced throughout the casting and backfill processes.

To avoid the excessive time and costs associated with the above-described header casting manufacturing processes, newer manufacturing methods have turned to injection molding the header about a connector assembly already welded to the housing, the injection molding of the header about the connector assembly resulting in a completed, or substantially completed, header connector assembly. However, unlike the atmospheric pressures of the above-described header casting manufacturing processes, injection molding processes subject the connector assembly to high pressures, which the connector receptacles of the connector assembly may not be able to withstand. This is especially the case with respect to IS4/DF4 quadripolar connector receptacles.

To facilitate the injection molding of the header about the connector assembly and is connector receptacles, novel and nonobvious configurations, systems and methods have been developed to allow the connector assembly, and especially its connector receptacles, to endure the high pressures of injection molding.

BRIEF SUMMARY OF THE INVENTION

Disclosed herein is an implantable pulse generator for administering electrotherapy via an implantable lead. In one embodiment, the pulse generator includes a housing and a header connector assembly coupled to the housing. The header connector assembly includes a connector assembly and a header enclosing the connector assembly. The connector assembly includes a support and a connector receptacle. The support extends at least partially about the connector receptacle and is at least partially responsible for having prevented injection molding material from entering the connector receptacle when the injection molding material was injection molded about the connector assembly in forming the header.

In one embodiment, the support was over-molded about the connector receptacle prior to the injection molding material being injection molded about the connector assembly. In another embodiment, the support was press-fit about the connector receptacle prior to the injection molding material being injection molded about the connector assembly.

In one embodiment, the connector receptacle is a quadripolar connector receptacle. The support includes at least one window positioned over a connector block of the quadripolar connector receptacle, and a conductor ribbon extends from a feedthru of the housing and through the window to electrically couple with the connector block.

The support may further include a circumferential rib of a sidewall of the support, the circumferential rib being immediately adjacent the window and covering an underlying insulating ring of the quadripolar connector receptacle. The circumferential rib may extend across in an axial direction, and along in a circumferential direction, the underlying insulating ring and, in so doing, provided a sealing mechanism to isolate the underlying insulating ring from the injection molding material when injection molded.

In one embodiment, the support may include at least one positioning feature that at least assisted in maintaining the position of a first component of the connector assembly relative to other components of the connector assembly when the injection molding material was injection molded about the connector assembly. The positioning feature may be in the form of a recess that mated with a tip block or ring block of the connector assembly. The positioning feature may have received a ribbon conductor of the connector assembly.

In one embodiment, the implantable pulse generator further includes a suture opening in the header connector assembly. The suture opening is defined solely by the injection molding material forming the header and not by any part of the connector assembly or housing.

Also disclosed herein is a method of manufacturing an implantable pulse generator for administering electrotherapy via an implantable lead. In one embodiment, the method includes: at least partially extending a support about a quadripolar connector receptacle to form a quadripolar subassembly; creating a connector assembly by coupling the quadripolar subassembly to other components of the connector assembly; creating a header connector assembly by injection molding a header about the connector assembly, the support being at least partially responsible for preventing injection molding material from entering the quadripolar connector receptacle when injection molding the header about the connector assembly; and coupling the header connector assembly to a housing.

In one embodiment, the at least partially extending the support about the quadripolar connector receptacle includes over-molding the support about the quadripolar connector receptacle. Alternatively, the at least partially extending the support about the quadripolar connector receptacle includes press-fitting the support about the quadripolar connector receptacle.

In one embodiment, the support includes at least one window positioned over a connector block of the quadripolar connector receptacle and coupling the quadripolar subassembly to other components of the connector assembly includes extending a conductor ribbon from a feedthru of the housing and through the window to electrically couple with the connector block.

In one embodiment, the support further includes a circumferential rib of a sidewall of the support, the circumferential rib being immediately adjacent the window and covering an underlying insulating ring of the quadripolar connector receptacle. The circumferential rib may extend across hi an axial direction, and along in a circumferential direction, the underlying insulating ring and, in so doing, provides a sealing mechanism to isolate the underlying insulating ring from the injection molding material when injection molded.

In one embodiment, the support includes at least one positioning feature that at least assists in maintaining the position of a first component of the connector assembly relative to the other components of the connector assembly when the injection molding material is injection molded about the connector assembly. The positioning feature may be in the form of a recess that mated with a tip block or ring block of the connector assembly. The positioning feature may receive a ribbon conductor of the connector assembly.

In one embodiment, formation of a suture opening in the header connector assembly is solely a function injection molding the header about the connector assembly such that no components of the header or connector assembly define the suture opening.

In one embodiment, at least partially extending the support about the quadripolar connector receptacle to form a quadripolar subassembly includes supporting multiple quadripolar connector receptacles on a jig and at least partially extending a respective support about each quadripolar connector receptacle. The at least partially extending a respective support about each quadripolar connector receptacle may occur in a parallel process.

While multiple embodiments are disclosed, still other embodiments of the present disclosure will become apparent to those skilled in the art from the following detailed description, which shows and describes illustrative, embodiments of the disclosure. As will be realized, the invention is capable of modifications in various aspects, all without departing from the spirit and scope of the present disclosure. Accordingly, the drawings and detailed description are to be regarded as illustrative in nature and not restrictive.

BRIEF DESCRIPTION OF THE DRAWINGS

FIG. 1A is an isometric view of a proximal end portion (i.e., lead connector end) of a conventional transvenous bipolar pacing lead, FIG. 1B is a side view of a proximal end portion lead connector end) of a conventional transvenous quadripolar pacing lead.

DETAILED DESCRIPTION

Figure 2A:
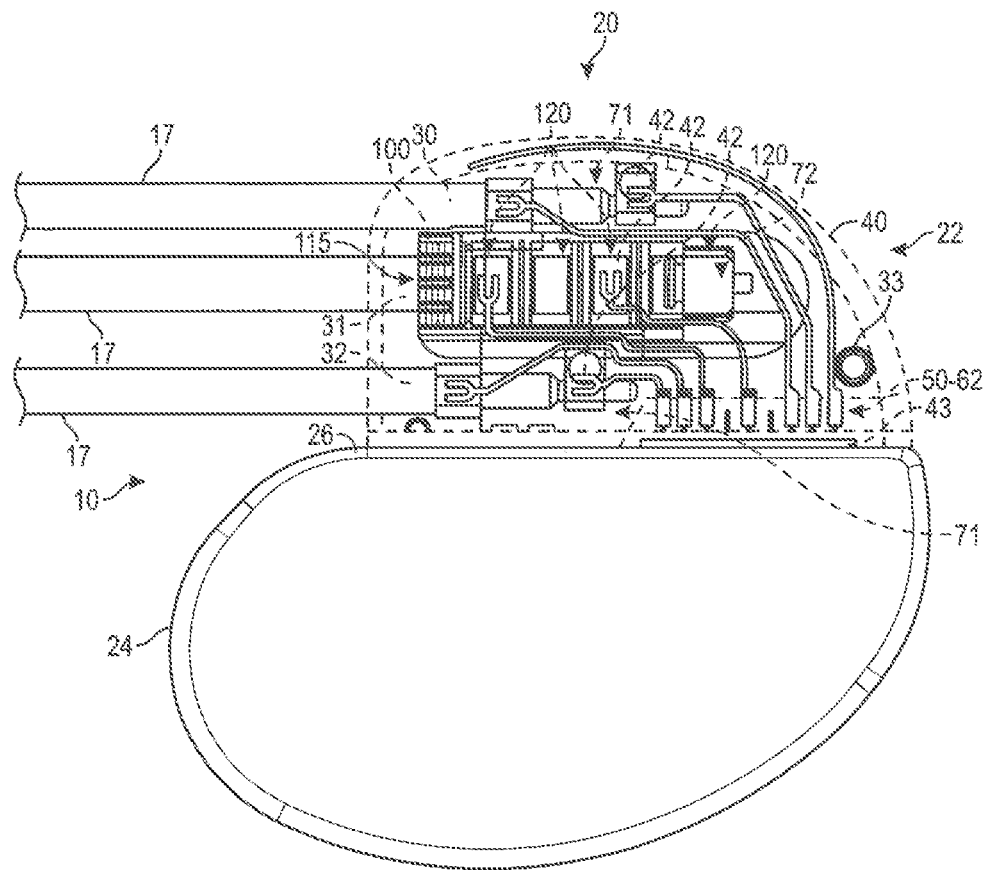
FIG. 2A is an isometric view of a cardiac pacemaker/defibrillator unit (i.e., implantable pulse generator (IPG)) incorporating connector junctions or terminals for communication with one or more electrodes.

Implementations of the present disclosure involve implantable pulse generator (IPG) 20 for administering electrotherapy or other neurostimulation via an implantable lead having a lead connector end 11 on a proximal end of the implantable lead 10. The FIG. includes a housing 24 or can and a connector assembly 42 enclosed in a header 40 to form a header connector assembly 22, which is coupled to the housing or can. The header 40 and connector assembly 42, combined as the header connector assembly 22, form at least one lead connector receiving bore 31 and associated receptacle 72 that includes electrical contacts that make electrical contact with corresponding electrical terminals. 12, 14 on the lead connector end 11 on the proximal end 10 of the implantable lead when the lead connector end is plugged into or otherwise received in the lead connector receiving bore and receptacle. Via the electrical connection between the corresponding electrical terminals of the lead connector end and the electrical contacts of the lead connector receiving receptacle, electrical signals can be administered from the FIG. and through the lead to patient tissue. Similarly, but in reverse, electrical signals originating in patient tissue can travel via the lead to the FIG. to be sensed at the IPG.

As disclosed in detail below, the connector assembly 42 forming the header connector assembly 22 of the IPG 20 employs a quadripolar subassembly 48, which includes a support 100 that encloses a quadripolar connector receptacle 72. The support 100, which may be over-molded or press-fit over the receptacle 72, is configured to resist the high pressures of injection molding the header 40 about the connector assembly 42, thereby enabling the efficient and predictable use of injection molding methods for creating the header connector assembly 22. Efficient injection molding of the header materials provides substantial cost and time savings over those FIG. configurations and methods of assembly that are associated with the traditional backfill process.

Before beginning a detailed discussion of the assembly of the header 40 and the connector assembly 42 enclosed therein to form the header connector assembly 22, which is mounted onto the housing 24, a general discussion is first given regarding features of a common lead connector end 11 at the proximal end 10 of an implantable medical lead followed by a general discussion of the features of an IPG 20 and components of its connector assembly 42.

A. General Overview of Lead Connector Ends, IPG and Aspects of IPG.

FIG. 1A shows a proximal end portion 10 of a conventional transvenous bipolar pacing lead, and FIG. 1B shows a proximal end portion 10 of a conventional transvenous quadripolar pacing lead. Both FIGS. 1A and 1B are generally representative of any type of implantable lead whether in the cardiac, pain management or other medical treatment space. For each of the leads, the diameter may be made sufficiently small to facilitate the lead's implantation into small veins such as those found in the coronary sinus region of the heart and to allow implantation of a plurality of leads into a single vessel for multi-site or multi-chamber pacing. It should be understood, however, that other lead designs may be used, for example, multipolar leads having proximal ends portions that are bifurcated, trifurcated or have other branched configurations.

While the lead proximal ends shown in FIGS. 1A and 1B are respectively of the bipolar and quadripolar variety, there are unipolar leads that carry but a single electrode and other multipolar leads that have other multiples of electrodes. Accordingly, the teachings herein, while discussed in the context of bipolar and quadripolar leads and compatible receptacles for receiving the same in a mechanically coupled and electrically connected arrangement with an IPG, should not be limited to bipolar or quadripolar arrangements, but should be considered to encompass all applicable lead and FIG. configurations, unless otherwise expressly limited in the patent claims associated with this Detailed Description.

As is well known in the art, bipolar and quadripolar coaxial leads typically consist of a tubular housing of a biocompatible, biostable insulating material containing an inner multifilar conductor coil that is surrounded by an inner Insulating tube. The inner conductor coil is connected to a tip electrode on the distal end of the lead.

The inner insulating tube is surrounded by one or more separate, outer multipolar coaxially arranged conductor coils also enclosed within the tubular housing. Each outer conductor coil is connected to a respective anodal ring electrode, or defibrillation coil, along the distal end portion of the lead.

The inner insulation is intended to electrically isolate the coaxial conductor coils from each other preventing any internal electrical short circuit, while the housing protects the entire lead from the intrusion of body fluids. More specifically, the inner insulating materials and outer housing materials are arranged in a coaxial arrangement with each other and with the coaxial conductor coils to provide electrical isolation between the coaxial coils, and electrically isolate the coaxial coils from the environment exterior the outer housing. These insulating materials are typically either silicone rubber, polyurethane, a combination thereof or other similar biocompatible materials.

In other configurations, there are bipolar or quadripolar leads in which multipolar cable conductors contained within multilumen housings are substituted for one or more of the coaxial conductor coils in order to reduce even further the overall diameter of the lead.

The proximal lead end portion 10 shown in FIG. 1A includes a bipolar lead connector end 11 that conforms to the IS1/DF1 standard, while the proximal lead end portion 10 shown in FIG. 1B includes a quadripolar lead connector end 11 that conforms to the IS4/DF4 standard. In each case, the lead connector end includes spaced-apart electrical terminals including a tip terminal 12 and one or more ring terminals 14, The tip terminal 12 is electrically connected via the inner conductor coil to the tip electrode at the distal end of the lead, while each ring terminal 14 is electrically connected to a respective anodal ring electrode, or defibrillation coil, at the distal end of the lead via a respective coaxial conductor coil. The tip and ring terminals of the lead connector end may each be engaged by a conductive garter spring contact or other resilient electrical contact element in a corresponding lead connector receptacle associated with a connector receiving bore of the header, the resilient electrical contact element being part of, and electrically connected to, a connector assembly enclosed in the header as described below.

As can be understood from FIGS. 1A and 1B, the lead connector end 11 on the proximal lead end portion 10 further comprises spaced-apart seal rings 16 for abutting against in a fluid-sealing manner the inner circumferential surface of the lead connector receiving bore of the header, thereby preventing body fluids from reaching the electrical terminals and contacts when the lead connector end 11 is plugged into the corresponding lead connector receiving bore and its lead connector receptacle. These seal rings 16 may also electrically and physically isolate the ring terminals 14 from each other, plus the ring terminals from the tip terminal 12. The lead body 17 can be seen to extend distally from the distal end of the lead connector end 11, the lead body supporting the tip electrode, ring electrodes, and defibrillation coil at the distal end of the lead.

Referring specifically to FIG. 16, in some embodiments and applications, the ring terminals, moving from left to right, may correspond to the ventricular pace sense ring connection, the right ventricle or RV coil connection, and the superior vena cave or SVC coil connection. The tip terminal 12 may correspond to the ventricular pace sense tip electrode connection.

Figure 3:
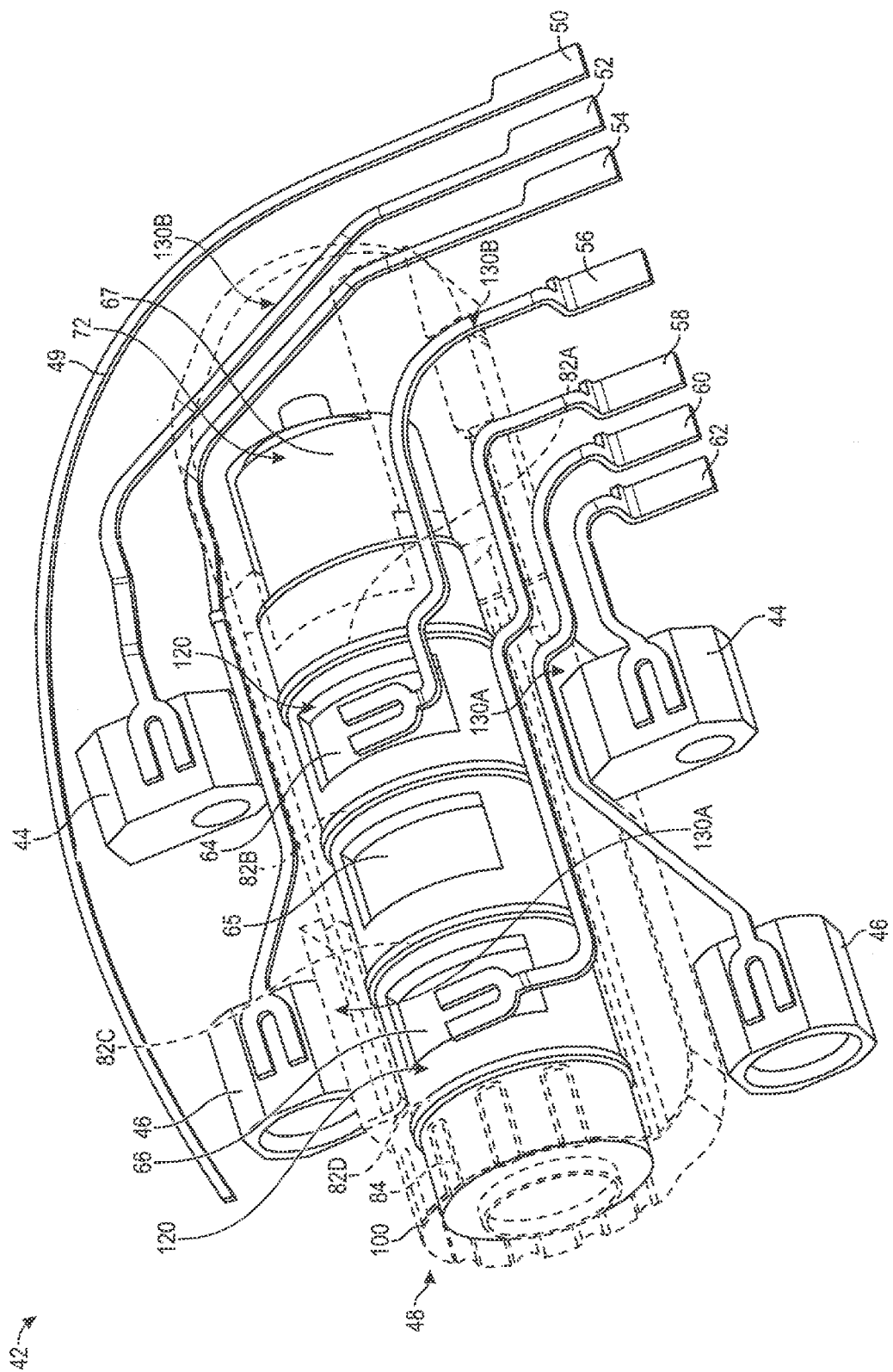
FIG. 3 is an isometric view of a connector assembly that resides in the header and therewith combines to form the header connector assembly of the FIG. of FIG. 2A.

As discussed in greater detail below with respect to FIG. 26, with the lead connector end 11 of the lead inserted in the lead connector receiving bore of the header connector assembly, the tip and ring terminals 12 and 14 are electrically coupled via the contacts of the lead receiving connector receptacle of the connector assembly and a feedthru to the electronic circuits within the hermetically sealed housing of the FIG. (e.g., cardiac pacemaker, ICD, or other implantable tissue stimulation and/or sensing device such as those used in pain management, etc.), FIG. 2A shows a multi-site or multi-chamber cardiac pacemaker/defibrillator unit that is generally representative of any type of IPG 20 incorporating a header connector assembly 22 coupled to a housing 24. The header connector assembly 22 includes a header 40 enclosing a connector assembly 42, which is depicted in FIG. 3 and discussed below. The IPG 20 is of a conventional design, including a hermetically sealed housing 24, which is also known as a can or casing. The housing 24 encloses the electronic components of the IPG 20 with the header connector assembly 22 mounted along a top edge 26 of the housing 24.

FIG. 2A illustrates that, in some embodiments, the header connector assembly 22 may include three or more lead connector receiving bores 30, 31 and 32 leading to respective connector receptacles for receiving the lead connector ends of three implantable leads. FIG. 2A also shows a lead body 17 extending from each bore 30, 31 and 32 wherein the respective lead connector end is plugged into, and received within, its respective connector receptacle. In other embodiments, the header connector assembly 22 may include less than three connector receptacles or more than three connector receptacles. In some embodiments, one or more of the connector receptacles may be in the form of an IS1/DF1 connector receptacle 71 for receiving the IS1/DF1 lead connector end 11 of FIG. 1A and/or an IS4/DF4 connector receptacle 72 for receiving the IS4/DF4 lead connector end 11 of FIG. 1B, For example, as shown in FIG. 2A and discussed in detail below, the IPG 20 may have two IS1/DF1 connector receptacles 71, which are aligned with bores 30 and 32, and one IS4/DF4 connector receptacles 72, which is aligned with bore 31. Of course, in other embodiments, the numbers, types and locations of each standard of connector receptacle may vary from what is shown in FIG. 2A.

As can be understood from FIGS. 1A, 2A and 3, the IS1/DF1 connector end 11 of FIG. 1A can be received in either of the bores 30 and 32 and by the corresponding IS1/DF1 connector receptacles 71. In doing so, the ring terminal 14 of the IS1/DF1 connector end 11 is received by, and electrically connected with, the ring block 46 (see FIGS. 1A and 3), and the tip terminal 12 is received by, and electrically connected with, the tip block 44 (see FIGS. 1A and 3). The seals 16 make circumferential sealing contact with the inner circumferential surface of the receiving bore 30, 32, as can be understood from FIGS. 1A and 2A, thereby preventing body fluids from reaching the electrical terminals and contacts when the lead connector end 11 is plugged into the bore 30, 32 and its connector receptacle 71.

Figure 2B:
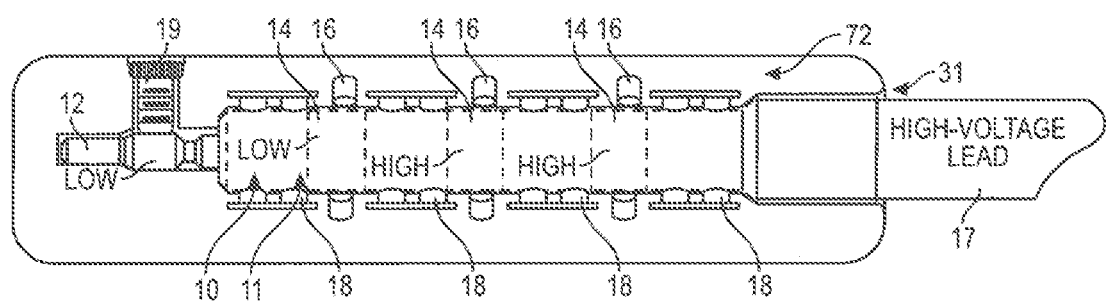
FIG. 2B is a side view of the IS4/DF4 lead connector end of FIG. 1B positioned within the IS4/DF4 quadripolar connector receptacle of the FIG. of FIG. 2A.

As seen in FIG. 2B, which is a side view of the IS4/DF4 lead connector end 11 of FIG. 1B positioned within the IS4/DF4 quadripolar connector receptacle 72 of the IPG 20 of FIG. 2A, the three ring terminals of the lead connector end 11 may each be engaged by a conductive garter spring contact 16 or other resilient electrical contact element in the quadripolar connector receptacle 72 of the header connector assembly 22. The tip terminal 12 may be engaged by a conductive set screw 19.

As illustrated in FIG. 28, the quadripolar connector receptacle 72 further includes spaced-apart seal rings 18 for abutting against in a fluid-sealing and electrically insulating manner the outer circumferential surface of respective seal rings 16 of the lead connector end 11, thereby preventing body fluids from reaching the electrical terminals and contacts when the lead connector end 11 is plugged into the bore 31 and its quadripolar connector receptacle 72.

As shown in FIG. 2A, the quadripolar connector receptacle 72 is part of the connector assembly 42 enclosed in the header 40. As can be understood from FIGS. 2A and 28, with the lead connector end 11 of the lead inserted hi the bore 31 of the quadripolar connector receptacle 72, the tip terminal 12 and ring terminals 14 are electrically coupled via the contacts 19, 16 of the quadripolar connector receptacle 72 and the feedthru 43 to the electronic circuits within the hermetically sealed housing of the IPG 20.

Figure 2C:
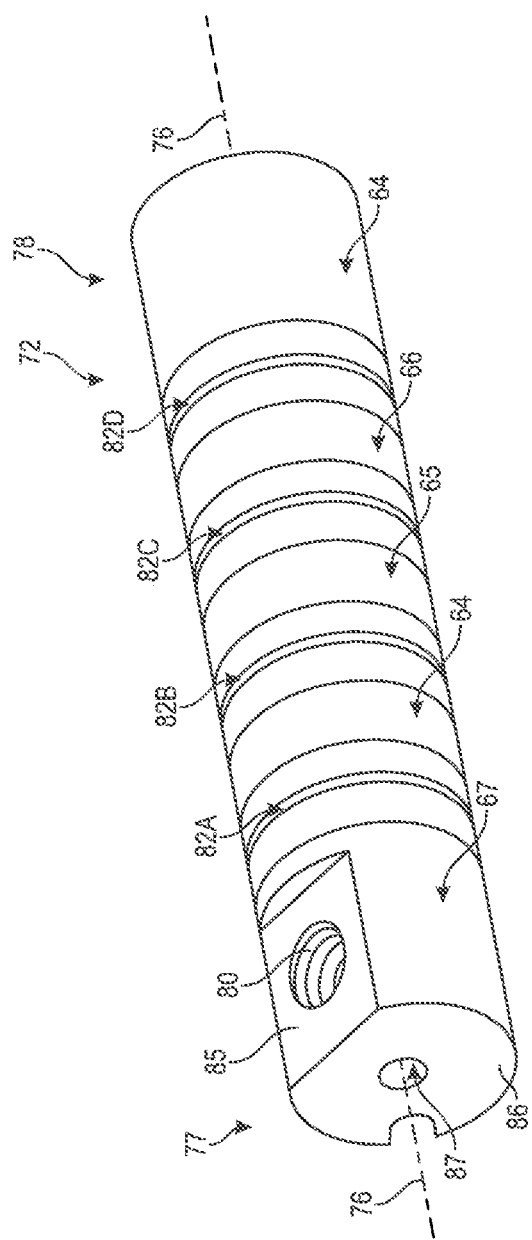
FIG. 2C is an isometric view of the IS4/DF4 quadripolar connector receptacle of FIG. 2A.

Reference is made to FIG. 2C, which is an isometric view of the quadripolar connector receptacle 72 of FIG. 2A. As illustrated in FIG. 2C, the quadripolar connector receptacle 72 extends along a longitudinal axis 76 between a proximal end 77 and a distal end 78, opposite the proximal end 77. At the proximal end 77 is a tip connector block 67, which may be made of steel or other biocompatible electrically conductive metal. The tip connector block 67 includes the set screw bore 80, which is threaded to receive a set screw 19, as depicted in FIG. 2B. Moving distally from the connector block 67, the quadripolar connector receptacle 72 includes a first insulating ring 82a, a first connector ring block 64, a second insulating ring 82b, a second connector ring block 65, a third insulating ring 82c, a third connector ring block 66, and a fourth insulating ring 82d. At the distal end 78 of the quadripolar connector receptacle 72 is an entrance ring block 84, which may be made of steel or other biocompatible metal.

The insulating rings 82a-d may be made from a reinforced polysulfone or similar material. The connector ring blocks 64-66 may be made from steel or other biocompatible electrically conductive metal. The outer surface of the quadripolar connector receptacle 72 may be cylindrical with the Up connector block 67, the entrance ring block 84, and the insulating rings 82a-d. The connector ring blocks 64-66 may have outer diameters that are about equal to each other, forming a generally uniform cylinder. The tip connector block 67 may include a planar, notched or recessed surface 85 that is about perpendicular from a planar proximal surface 86. A terminal Up receiving bore 87, which is configured to receive the tip terminal 12 as illustrated in FIG. 23, is centered on the planar distal surface 86 and extends along the longitudinal axis 76 into an inner opening within the quadripolar connector receptacle 72.

As can be understood from FIGS. 13, 2A, 23 and 2C, in the context of an IS4/DF4 lead connector end 11 being received in an IS4/DF4 quadripolar connector receptacle 72, the Up connector block 67 is configured to receive and make electrical contact with the tip terminal 12 of a lead connector end 11. Similarly, each connector ring block 64, 65, 66 is configured to receive and make electrical contact with its respective ring terminal 14 of the lead connector end 11.

As shown is FIG. 3, which is an isometric view of a representative connector assembly 42 of the header connector assembly 22 of the IPG 20 of FIG. 2A, the connector assembly 42 includes tip blocks 44, ring blocks 46, and a quadripolar subassembly 48, among other structures and components. The quadripolar subassembly includes an overmolded support 100 surrounding the quadripolar connector receptacle 72 discussed above with respect to FIG. 2C. As discussed above with respect to FIG. 2C, the quadripolar connector receptacle 72 includes quadripolar components such as first, second and third quadripolar ring blocks 64, 65 and 66, and the tip block 67, which may include a conductive and securing arrangement like that of the setscrew 19 of FIG. 2B.

As discussed above with respect to FIG. 2C, the ring blocks 46 and quadripolar ring blocks 64, 65, 66 may include spring contacts or other resilient contacting arrangements. As can be understood from FIG. 3, each electrical block 44 and 46 of the connector assembly 42 serves as an electrical contact of the connector assembly 42. This is also the case with the electrical blocks 64, 65, 66 and 67 of the quadripolar subassembly 48. Thus, as can be understood from FIGS. 1A, 1B, 2A, 2B, 2C and 3, each tip block 44, 67 is configured to receive and make electrical contact with the tip terminal 12 of a lead connector end 11 received in the corresponding bore 30, 31 and 32 of the header 40. Similarly, each ring block 46, 64, 65, 66 is configured to receive and make electrical contact with the ring terminal 14 of a lead connector end 11 received in the corresponding bore 30, 31 and 32 of the header 40. While the connector assembly 42 of FIG. 3 is of an IS4/DF4 configuration for at least the quadripolar connector receptacle 72 associated with bore 31, other configurations (e.g., IS1/DF4, etc.) are used in other embodiments, including the IS1/DF1 connector receptacles 71 associated with bores 30 and 32, While the connector assembly 42 of FIG. 3 only depicts two pairs of blocks 44, 46, plus those blocks 64, 65, 66 of the quadripolar subassembly 48 discussed below, in other embodiments there may be less or more pairs of blocks 44, 46 and/or less or more quadripolar subassemblies 48.

As shown in FIG. 3, the connector assembly 42 also includes an antenna 49, a an RF anchor tab 50, an A-tip tab 62, an A-ring tab 54, a first quadripolar block tab 56, a second quadripolar block tab 58, a RV-tip tab 60, and a RV-ring tab 62 and other conductors that extend between the various tabs and their respective electrical contacts of the connector assembly or other components thereof. As can be understood from FIG. 2A, the various tabs 52-62 are welded to corresponding terminals of a feedthru 43 extending from circuitry of the IPG 20 contained in the housing 24 of the IPG 20 when the header connector assembly 22 is joined with the housing 24 to form the IPG 20. The connector assembly 42 is manufactured of materials and via methods known in the industry. The connector assembly 42 is injection or otherwise molded into the header 40 to form the header connector assembly 22 of FIG. 2A.

As illustrated in FIG. 2A, the header connector assembly 22 may have room for a suture opening 33 through the header 40. The suture opening may receive a suture for securing the IPG 20 in the patient when being implanted. The space available for the suture opening 33 is at least partially on account of the advantageous configuration of the connector assembly 42 made possible by the quadripolar subassembly 48, which provides for more unoccupied space within the header as compared to connector assemblies of past configurations. Further, as can be understood from A. 2A, in one embodiment, the suture opening 33 is defined solely by injection molding material forming the header 40 and not by any part of the connector assembly 42 or housing 24.

As described in detail below, the header 40 is injection molded about the connector assembly 42 to form the header connector assembly 22, which is connected to the can 24 and therewith forms the IPG 20, as can be understood from FIG. 2A. Unlike conventional backfilling procedures and casting of the connector assembly within the header, which is done at atmospheric pressure and results in minimal stresses on the components of the connector assembly, the injection molding process may subject the connector assembly 42 to high pressures of about 20,000 pounds per square inch ("psi"). Conventional IS4/DF4 quadripolar connector receptacles 72 and the associated connector assemblies 42 are not designed to withstand such pressures, and if conventional IS4/DF4 quadripolar connector receptacles 72 and the associated connector assemblies 42 were subjected to such pressures, a number of problems would likely occur. First, the insulating rings 82a-d, which typically have a low yield strength, would likely deform or buckle under injection molding pressures. The deformed insulating rings 82a-d would allow the injected molten material (e.g., tecothane, pallethane, etc.) to leak inside the IS4/DF4 quadripolar connector receptacles 72 and other components of the associated connector assemblies 42, which would create bubbles in the molded header 40. The leakage into the components of the connector assembly 42 may prevent electrical connections between the lead connector end 11 and the various blocks 44, 46 and 64-67 of the connector assembly 42 or may prevent insertion of the lead connector end 11 into the bores 30-32 and the corresponding connector receptacles, such as the IS4/DF4 quadripolar connector receptacle 72, among other potential problems.

The quadripolar subassembly 48 and, more specifically, its over-molded support 100 are capable of withstanding the pressures subjected by the injection molding process of the header 40 around the connector assembly 42, thereby facilitating the injection molding process in the manufacture of the header connector assembly 22. A detailed discussion of the quadripolar subassembly 48 and its over-molded support 100, manufacture and advantages now follows.

B. Quadripolar Subassembly With Over-molded Support Surrounding Quadripolar Components.

Figure 4:
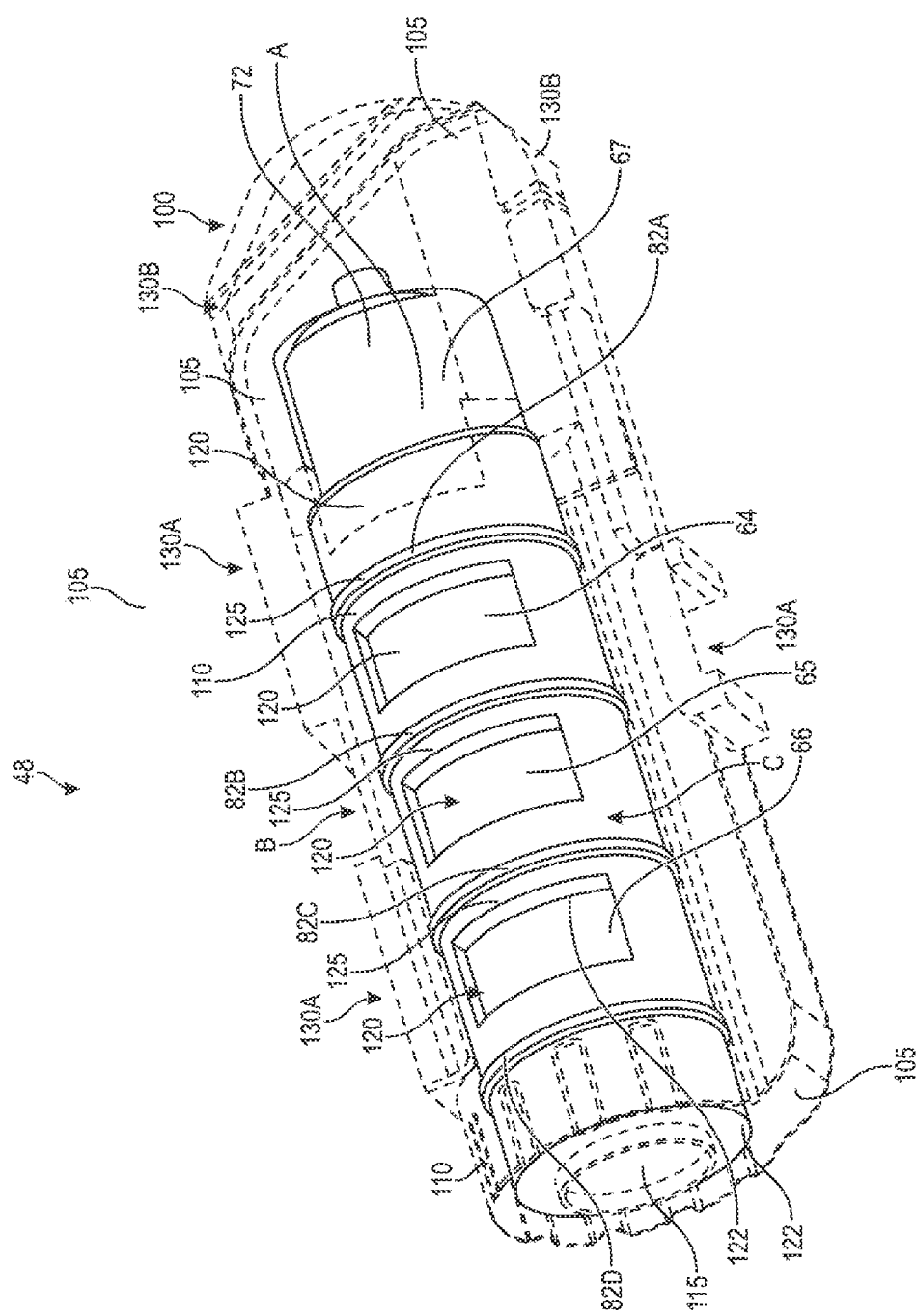
FIG. 4 is an isometric view of a quadripolar subassembly including an over molded support surrounding the IS4/DF4 quadripolar connector receptacle of FIG. 2C, the quadripolar subassembly forming part of the connector assembly of FIG. 3.

The quadripolar connector receptacle 72 described above with respect to FIGS. 2A-2C, is a four connection lead receptacle that offers additional vectors within either the low voltage or high voltage IPG 20. When stacked in a row axially, the components 64-67 and 82a-b of the IS4/DF4 quadripolar connector receptacle 72 must remain intact as pre-defined by the components and industry standards. The pressures of the injection molding process pose a risk for the quadripolar connector receptacle 72 to stay intact and assembled, FIG. 4 is an isometric view of the quadripolar subassembly 48 of FIG. 3. To address the risk presented by the high pressures of injection molding, the quadripolar subassembly 48 includes an over-molded support 100 surrounding the quadripolar connector receptacle 72. The over-molded support 100 is a pre-molded support configured to resist the pressure of the injection molding of the header 40 about the connector assembly 42 in forming the header connector assembly 22, as reflected in FIG. 2A. The over-molded support 100 facilitates a mechanically controlled molding process with precision tooling to control both the axial pressure and the hoop stress loading pressure which would radially enter between component seals 82a-d of the quadripolar connector receptacle 72. The quadripolar subassembly 48, with its over-molded support 100, is molded, along with the rest of the connector assembly 42, into the material of the header 40 in forming the overall header connector assembly 22, which is attached to the can 24 of the IPG 20.

Figure 5:
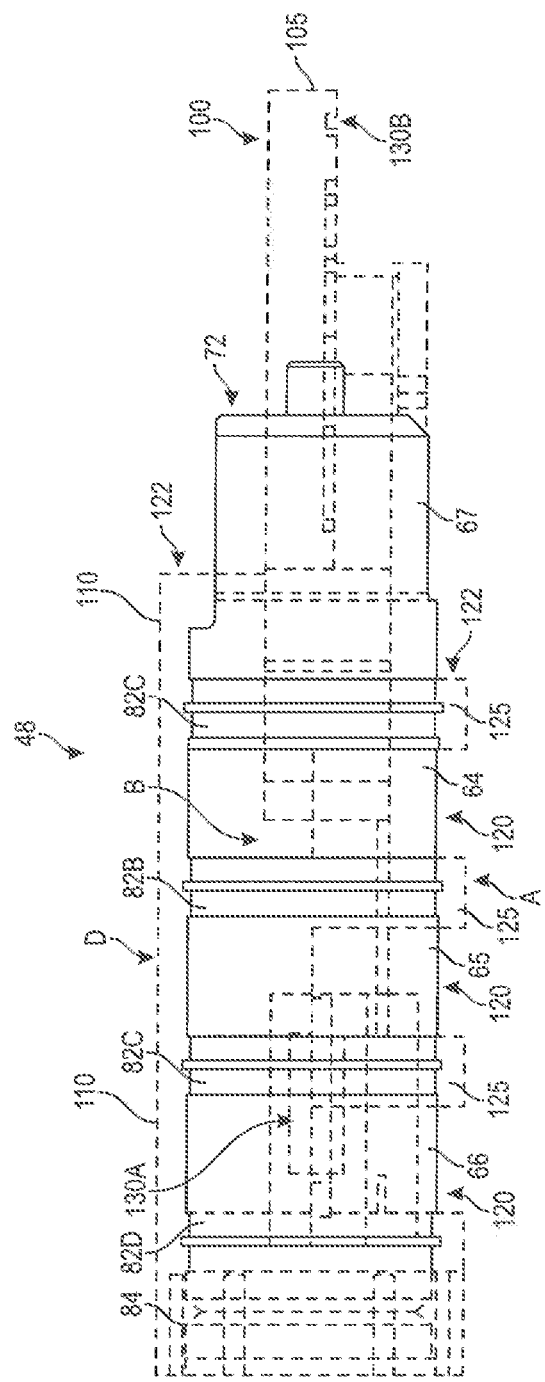
FIG. 5 is a top view of the quadripolar subassembly of FIG. 4.

As can be understood from FIG. 4 and also FIG. 5, which is a top view of the quadripolar subassembly 48, the quadripolar connector receptacle 72, as discussed in great detail above with respect to AGS. 2B and 2C, is a stack of five metallic components 64-67 and 84 and four silicone seal assemblies 82a-d interspersed between the five metallic components. The four metallic contact blocks 64-66 make electrical contact with corresponding contacts 14, 12 of the lead connector end 11 of the lead proximal end 10 (shown in FIG. 1B) when received in the quadripolar receptacle 72 associated with bore 31 of the header connector assembly of the IPG 20, as reflected in FIG. 2A. The four seal assemblies 82a-d are sandwiched between adjacent metallic component blocks 64-67 and 84 and interface with the seals 16 of the lead connector end 11 to isolate electrical pulses and/or high voltage shock therapy provided through electrical contacts made between the four metallic contact blocks 64-67 and corresponding contacts 14, 12 of the lead connector end 11, Obviously, the integrity of the seals plus the dimensional preciseness and consistency of the bore extending through the quadripolar connector receptacle 72 are paramount in the finished IPG 20.

As shown in AGS. 4 and 5, in one embodiment, the over molded support 100 includes a flange-like outer border 105 extending about a cylindrical portion 110 that encloses the quadripolar connector receptacle 72. The cylindrical portion 110 includes a distal bore opening 115 that is coaxially aligned with the bore of the quadripolar connector receptacle 72, and the bore 31 of the header connector assembly 22, as can be understood from FIGS. 2A and 4.

As indicated in FIGS. 4 and 5, at the location of one or more of the electrical block 64, 65, 66 and 87 of the quadripolar connector receptacle 72, the cylindrical portion 110 includes a window opening 120 that extends through the sidewall 122 of the cylindrical portion 110 to fully expose at least a portion of the corresponding electrical block 64, 65, 66 and 67. As can be understood from FIGS. 2A and 3, on account of these windows 120, the conductors of the connector assembly 42, which lead from the respective tabs 58, 56 and the feedthru 43 of the housing 24, can be welded to the respective electrical blocks 66, 64 of the quadripolar connector receptacle 72 in manufacturing the connector assembly 42 and prior to the header 40 being injected molded about the connector assembly 42.

As illustrated in FIGS. 4 and 5, in one embodiment, the windows 120 are located in a circumferential side quadrant (indicated by arrow A). The windows 120 are positioned such that they define circumferential ribs 125 in the sidewall 122 of the cylindrical portion 110, and these circumferential ribs 125 fully cover and extend about the outer cylindrical surface of each respective seal assembly 82a-d, both circumferentially and lengthwise. Where the windows 120 are not present, the sidewall 122 fully covers the lengthwise entirety of the quadripolar connector receptacle 72 along the top, bottom and remaining side circumferential quadrants of the quadripolar connector receptacle 72, as indicated by arrows B, C and D in FIGS. 4 and 5.

As depicted in FIGS. 4 and 5, the over-molded support 100 includes positioner features 130a, 130b that may be used to position and even retain or secure components of the connector assembly 42 in place during the manufacturing process. For example, the positioner features 130a, 130b can be used to maintain positions of components relative to each other during the welding process. Specifically, the positioner features 130a, 130b maintain the relative position of the IS4/DF4 connector receptacle 72 relative to the ribbon conductors leading from the tales 56, 58 to the first and second IS4/DF4 blocks 64, 66 as the ribbon conductors are welded to those blocks 64, 66. Similarly, the other blocks 44, 46 and the ribbons leading to those blocks 44, 46 may also be maintained in position relative to each other via the positioner features 130a, 130b during the welding of those ribbons to those blocks 44, 46.

Additionally, the positioner features 130a, 130b may be used to maintain the position of components relative to each other as the header 40 is injection molded about the connector assembly 42, as can be understood from FIGS. 2A and 3. Specifically, as shown in FIG. 3, positioner features may be in the form of block positioning features 130a and conductor positioning features 130b, whereby corresponding components of the connector assembly 42 reside at least partially within and/or extend along and/or pass through the respective positioning features 130a-b. For example, block positioning features 130a in the form of mating voids/openings/recesses can be seen to receive and at least assist in positioning and/or retaining blocks 44 and 46 in FIG. 3. The shapes of these mating voids/openings/recesses 130a may have surfaces that are three dimensional surfaces that are a surface negative of the corresponding block 44, 46 to be received in the block positioning feature 130a In a similar fashion, conductor positioning components 130b in the form of slots/notches/grooves receive and at least assist in positioning and/or retaining conductors extending from at least tabs 52 and 56 in FIG. 3.

In some cases, the ribbon conductors may be press-fit into respective conductor positioning features 130b such that a friction fit engagement exists between the conductor ribbon and its positioning feature 130b. Similarly, the blocks 44, 46 may be press-fit into respective block positioning features 130a such that a friction fit engagement exists between the block 44, 46 and its positioning feature 130a.

Figure 6:
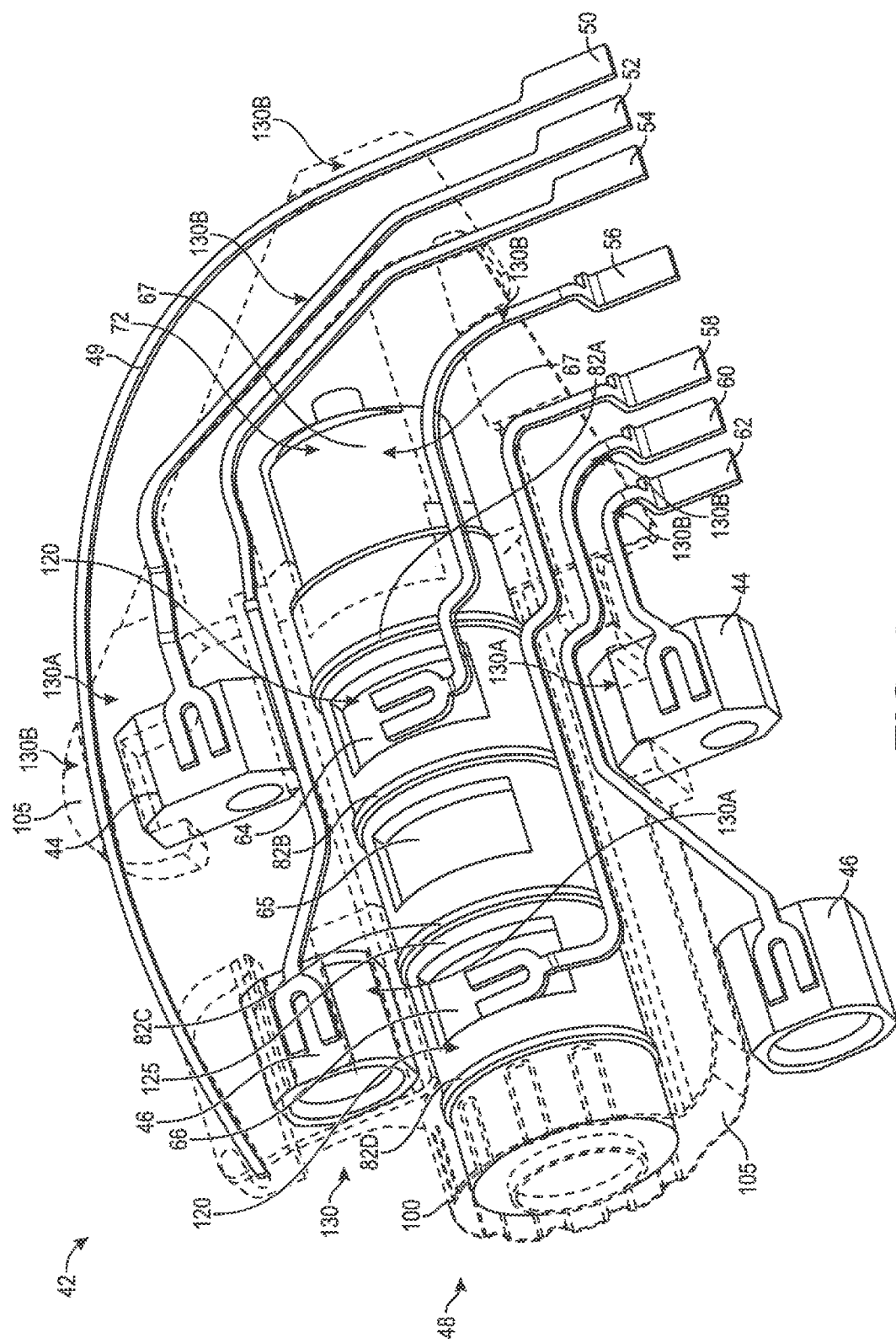
FIG. 6 is an isometric view of a quadripolar subassembly including an over-molded support surrounding the IS4/DF4 quadripolar connector, the quadripolar subassembly forming part of the connector assembly, and the over-molded support having additional and more encompassing positioning features as compared to the over-molded support of FIG. 3.
Figure 7:
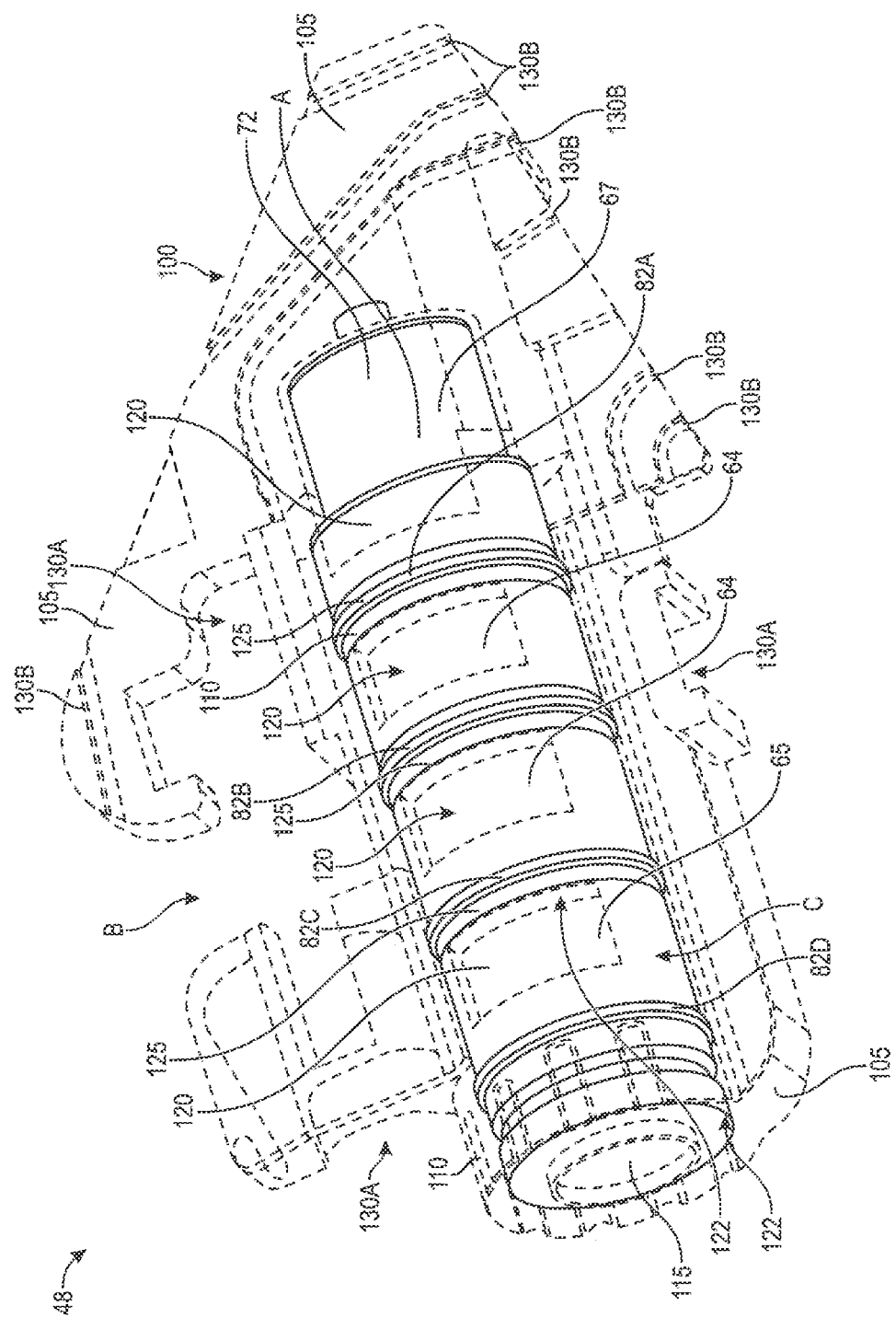
FIG. 7 is a top view of the quadripolar subassembly of FIG. 4.

FIGS. 6 and 7 are the same respective views as FIGS. 3 and 4, except of a second embodiment of the over-molded support 100. A comparison of the second embodiment of the over-molded support 100 of FIGS. 6 and 7 to the first embodiment of the over-molded support 100 of FIGS. 3 and 4 reveals that, in general, all aspects of the first and second embodiments are the same, except the flange-like outer border 105 is both more laterally extensive for the second embodiment and includes a greater number of positioning features 130a, 130b. Further, in some instances, the block positioning features 130a of the second embodiment more fully encompass about their respective blocks 44, 46.

Figure 8:
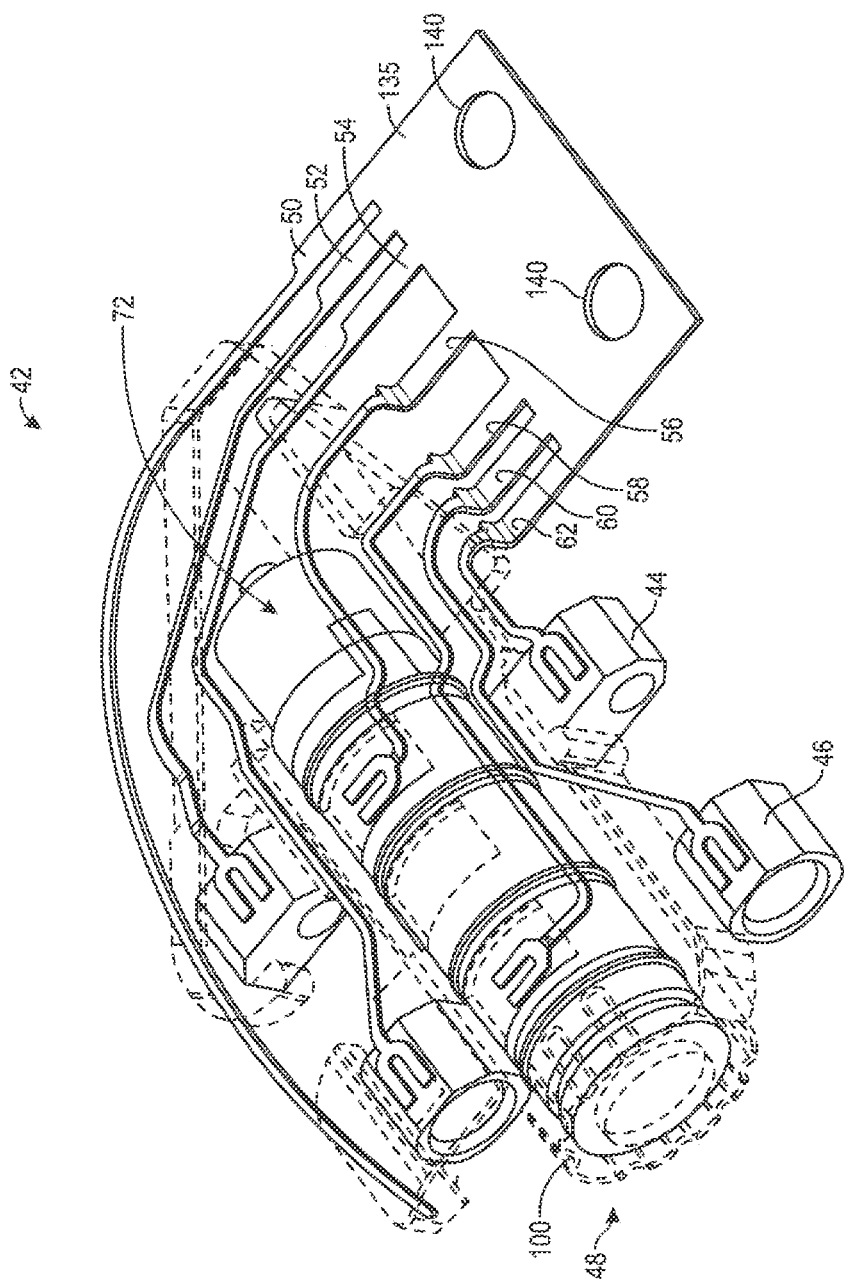
FIG. 8 is the same view as FIG. 6, except a ribbon retention feature extends as a rectangular plate from the bottom ends of the tabs.

FIG. 8 is the same view as FIG. 6, except a ribbon retention feature 135 extends as a rectangular plate from the bottom ends of the tabs 52-62. The ribbon retention feature 135 may be the same thickness as the ribbon forming the tabs 52-62 and may include one or more openings 140 defined through its thickness. The openings 140 may be circular or of another geometric shape. The ribbon retention feature 135 may be used to maintain the position of the tabs relative to each other during the injection molding of the header 40 about the connector assembly 42 in the manufacture of the header connector assembly 22. The ribbon retention feature 135 may also be used to locate the connector assembly 42 of FIG. 8 within the mold used to injection mold the header 40 about the connector assembly 42 in the formation of the header connector assembly 22.

Figure 9A:
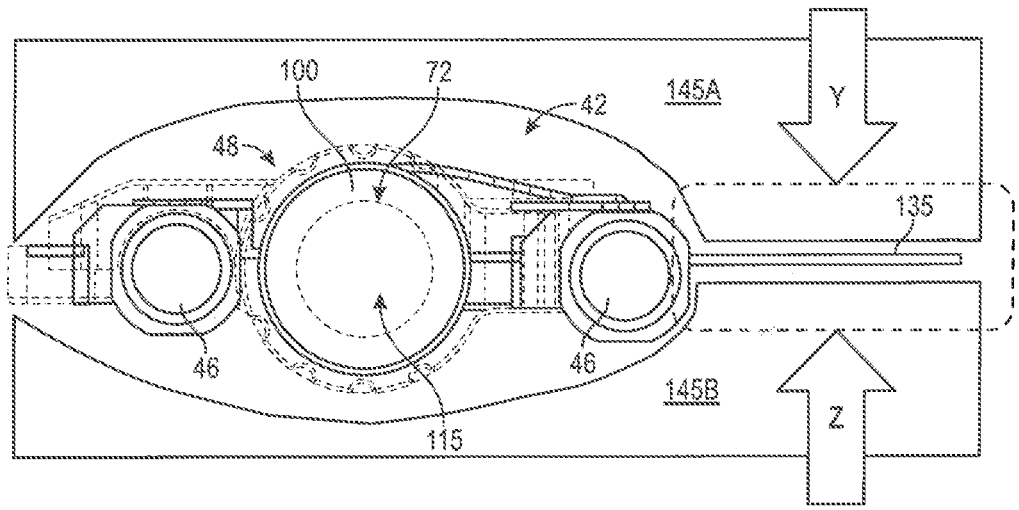
FIGS. 9A and 9B are end views of the connector assembly of FIG. 8 positioned between different versions of molding halves used in the injection molding process for forming the header about the connector assembly to form the header connector assembly.
Figure 9B:
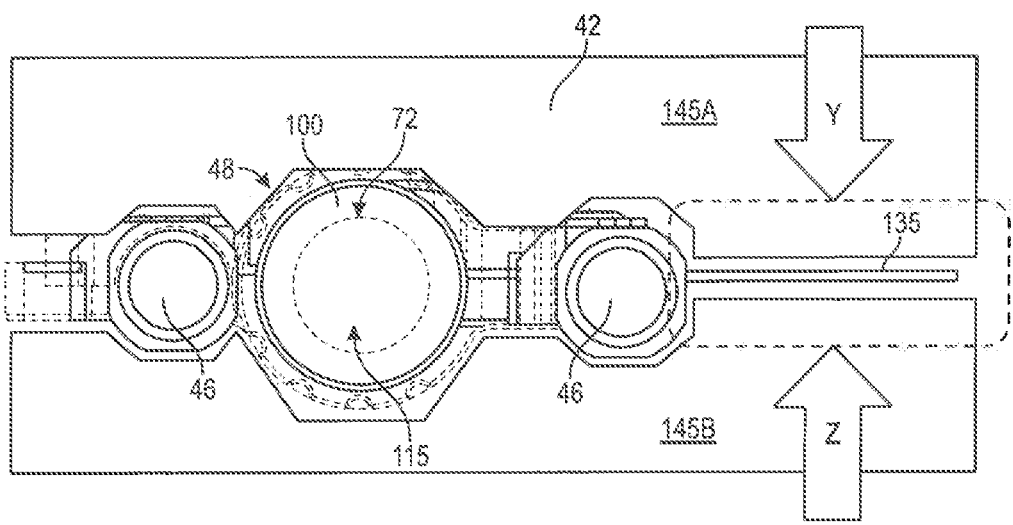

FIGS. 9A and 9B are end views of the connector assembly 42 of FIG. 8 positioned between different versions of molding halves 145a, 145b used in the injection molding process for forming the header 40 about the connector assembly 42 to form the header connector assembly 22. In one embodiment, as shown in FIG. 9A, the ribbon retention feature 135 is directly sandwiched between the upper and lower molding halves 145a-b as indicated by compressive force arrows Y and Z, but the connector assembly 42 has no dependency on the molding halves 145a-b. In another embodiment, as shown in FIG. 9B, the ribbon retention feature 135 is again directly sandwiched between the upper and lower molding halves 145a-b as indicated by compressive force arrows Y and Z, but the molding halves 145a-b make direct contact with the connector assembly.

C. Manufacturing a Header Connector Assembly Including a Quadripolar Subassembly With Over-molded Support Surrounding Quadripolar Components.

Figure 10:
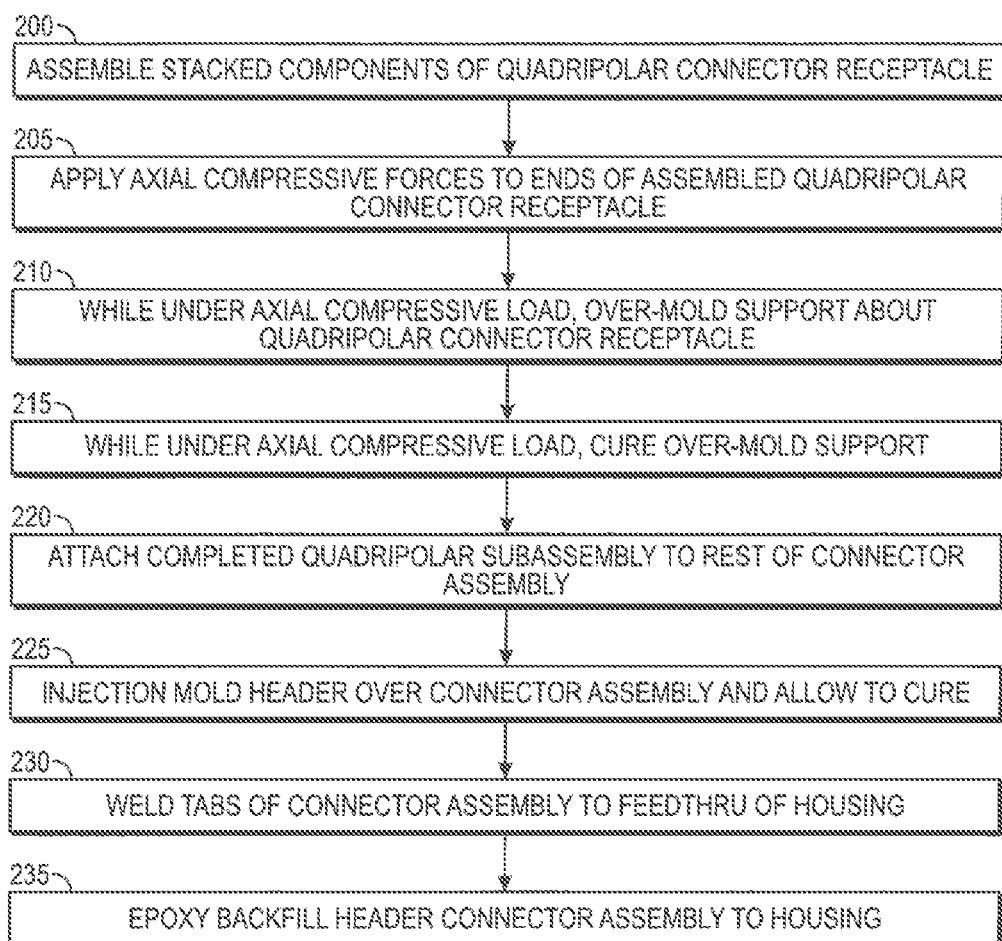
FIG. 10 outlines a method of manufacturing a header connector assembly that has a quadripolar subassembly that employs an over-molded support surrounding the components of an IS4/DF4 quadripolar connector receptacle.

FIG. 10 outlines a method of manufacturing a header connector assembly 22 that has a quadripolar subassembly 48 that employs an over-molded support 100 surrounding the components of an IS4/DF4 quadripolar connector receptacle 72. As indicated in FIG. 10 and can be understood from FIGS. 4, 5 and 7, the components 64-66, 84 and 82a-d of the IS4/DF4 quadripolar connector receptacle 72 are axially stacked together [BLOCK 200]. An axial compressive force is applied to the proximal and distal ends of the stacked together components [BLOCK 205]. The axial compressive force will be substantial enough to sufficiently seal between adjacent components 64-66, 84 and 82a-d against the pressure of the molding of the over-molded support 100 about the assembled quadripolar connector receptacle 72. External tooling may be used to provide the axial compression. In one embodiment, the external tooling is integrated with the molding tooling used to mold the over-molded support 100.

While the assembled quadripolar connector receptacle 72 is subjected to the axial compressive forces, the over-molded support 100 is molded over the assembled quadripolar connector receptacle 72 [BLOCK 210]. The molding process of the over-molded support 100 about the quadripolar connector receptacle 72 may take place via a variety of molding/casting processes known in the art, including injection molding. The over-molded support 100 may be formed of material compatible with the final header material and the components of the connector assembly 42, including those of the quadripolar connector receptacle 72. Such compatible materials for the formation of the over-molded support 100 may include thermoplastics, non-conductive ceramic, epoxy, and/or etc.).

While the assembled quadripolar connector receptacle 72 is still subjected to the axial compressive forces, the newly created over-molded support 100 is allowed to set/cure about the quadripolar connector receptacle 72 [BLOCK 215]. Once the material is cured/set, the completed quadripolar subassembly 48 (depicted in FIGS. 4 and 7) can be removed from the mold and stored for future incorporation into a lead connector assembly 42, such as those depicted in FIGS. 3 and 6.

Individual quadripolar subassemblies 48 can be created one at a time via serial application of the steps of BLOCKS 200-215. Alternatively, multiple quadripolar subassemblies 48 can be created via parallel operation of the steps of BLOCKS 200-215 by holding multiple axially compressed quadripolar connector receptacles 72 on a single jig and creating an over-molded support 100 about each axially compressed quadripolar connector receptacle 72 held by the jig, the over-molding of the supports 100 about their respective receptacles 72 occurring at the same time in parallel. Thus, via this parallel generation of the quadripolar subassemblies 48, six, 12 or any other number of multiples of the quadripolar subassemblies can be generated, allowed to cure/set, and pulled off of the jig and placed in storage until individually needed for combining with other components of a connector assembly 42, as discussed below.

While this manufacturing methodology has been outlined so far in the context of molding the over-molded support 100 about the quadripolar connector receptacle 72, in alternative embodiments, the support 100 may be in the form of a clamshell arrangement that is press-fit over the quadripolar connector receptacle 72. Such a press-fit embodiment of the support 100 may apply adequate compression about the receptacle 72 to provide sealing that can resist the high pressures of the following injection molding process, in some embodiments, the ability of the support 100 to resist the injection molding pressures may be enhanced by using materials for the support 100 that lend themselves to sealing (e.g., the materials are semi-resilient to form a seal against a subsurface), or the support 100 may employ O-rings or other sealing members between the underlying surface of the quadripolar connector receptacle 72 and the overlying aspects of the press-fit support 100 in the regions of the circumferential ribs 125. Such a press-fit support 100 could also provide adequate axial compressive force to maintain the components of the receptacle 72 sandwiched together.

As discussed above, the windows 120 of the completed quadripolar subassembly 48 of FIGS. 4 and 7 allow the metallic contact connector blocks 64-67 of the quadripolar connector receptacle 72 to be exposed for access to weld ribbons or wires to continue the electrical connection through the header connector assembly 42 to the feedthrough connections 43. Although the windows 120 expose the blocks 64-67, the adjacent circumferential ribs 125 in the sidewall 122 of the cylindrical portion 110 of the over-molded support 100 fully cover and extend about the outer cylindrical surface of each respective seal assembly 82a-d of the assembled quadripolar connector receptacle 72, both circumferentially and lengthwise to provide adequate protection against the forces of the injection molding process used to form the header 40 about the connector assembly 42 to form the header connector assembly 22 of FIG. 2A. The windows 120 and adjacent circumferential ribs 125 are formed through the molding process used to form the over-molded support 100 about the assembled quadripolar connector receptacle 72.

Referring again to FIG. 10, the completed quadripolar subassembly 48 is attached to the rest of the components of the connector assembly 42 [BLOCK 220]. Specifically, the blocks 44, 46 may be held in place via the block positioning features 130a (as indicated in FIGS. 3 and 6), the ribbon conductors leading from the tabs 50-62 may be held in place via the conductor positioning features 130b (as shown in FIGS. 3 and 6), and the ribbon conductors leading from the tabs 56, 58 may be welded to the blocks 64, 66 of the quadripolar connector receptacle 72 encompassed by the over-molded support 100 of the quadripolar subassembly 48.

The completed connector assembly 42 of FIG. 8 may be placed between the mold halves 145a-b with the ribbon retention feature 135 sandwiched between the mold halves 145a-b and the rest of the connector assembly 42 positioned between the mold halves 145a-b according to the arrangement of FIG. 9A or 9B. As discussed above, FIG. 9B depicts active header support integration. On the other hand, FIG. 9A depicts not incorporating support which benefits the header connector assembly's final second shot appearance and consistency without the complexities of exposed paths or orifice, which require a second or third process.

Once the connector assembly 42 is placed in the mold, the material of the header 40 is then injection molded about the connector assembly 42 and allowed to cure [BLOCK 225]. This header material may be tecothane, elastane, pallethane, or etc., as known in the art. The ribbon retention feature 135 is removed from the tabs 50-62. The tabs 50-62 may then be welded to the feedthru 43 [BLOCK 230], and the completed header connector assembly 22 coupled to the housing 24 to form the IPG 20. The coupling of the header connector assembly 22 to the housing may occur via epoxy backfill [BLOCK 235].

As can be understood from FIG. 2A, in one embodiment, the formation of the header 40 via the injection molding of header material about the connector assembly 42 may be solely a function of injection molding the header material in a mold that defines the suture opening 33. In other words, no other aspect of the housing 24 or the header connector assembly 22, including its connector assembly 42 or any component of the header 40, is required to form the suture opening 33 in the header 40 or the resulting header connector assembly 22. All that is necessary is that the mold used in the injection molding process has a feature that will define the suture opening 33 in the resulting header 40 when the header material is injection molded about the connector assembly 42 during the injection molding process. Thus, it can be said that the suture opening 33 may be solely a function of header formation via injection molding of the header material about the connector assembly 42. In other words, the suture opening 33 in the header connector assembly 22 is defined solely by the injection molding material forming the header 40 and not by any part of the connector assembly 42 or housing 24.

In other embodiments, the connector assembly 42 and/or the housing 24 may include a component that assists in forming the suture opening 33 much in the same manner as the above-described suture opening defining feature of the mold that receives the injection molding of the header material. In such an embodiment, the component of the connector assembly 42 and/or housing 24 that ends up helping to define the suture opening 33 will end up being molded into the header material as part of a surrounding structure that, at least in part, defines, or assists in defining, the suture opening 33 in the completed header 40. Thus, in such an embodiment, it cannot be said that the suture opening 33 is solely a function of header formation via injection molding of the header material about the connector assembly 42.

One of the useful aspects disclosed herein is to retain and constrain the components of a quadripolar connector receptacle 72 of a pre-molded header connector assembly 22. The constraint allows for improved welding and sealing capabilities between process steps of the normal pre-molded header manufacturing process. By doing this, fewer steps are required to create the subassembly components (e.g., connector assembly 42 and header connector assembly 22) and reduce the cost and potential quality risks associated with additional processing steps.

Positioning features 130a, 130b may include interactions with neighboring components which enhance the location and positioning capabilities of the over-molded structure 100. Depending on the embodiment, the dimensions of the bore 31 leading to the quadripolar connector receptacle 72 may or may not be incorporated within the region of the over-molded structure 100.

While the subassembly 48 and its configuration and manufacture are discussed in the context of a support 100 being placed over an IS4/DF4 connector receptacle 72 and then the subassembly 48 being combined with a connector assembly 42 followed by the injection molding of a header 40 about the connector assembly to form the header connector assembly 22, these teachings are applicable to connector receptacles of other standards, including, but not limited to, IS1/DF1 connector receptacles.

The foregoing merely illustrates the principles of the invention. Various modifications and alterations to the described embodiments will be apparent to those skilled in the art in view of the teachings herein. It will thus be appreciated that those spilled in the art will be able to devise numerous systems, arrangements and methods which, although not explicitly shown or described herein, embody the principles of the invention and are thus within the spirit and scope of the present invention. From the above description and drawings, it will be understood by those of ordinary skill in the art that the particular embodiments shown and described are for purposes of illustrations only and are not intended to limit the scope of the present invention. References to details of particular embodiments are not intended to limit the scope of the invention.

What is claimed is:

1. An implantable pulse generator for administering electrotherapy via an implantable lead, the implantable pulse generator comprising:
    a housing; and
    a header connector assembly coupled to the housing, the header connector assembly including a connector assembly and a header molded about the connector assembly such that the header encloses the connector assembly,
    wherein the connector assembly includes a support and a connector receptacle, the connector receptacle extending along a longitudinal axis from a proximal end of the connector receptacle to a distal end of the connector receptacle and comprising connector ring blocks alternating with insulating rings in a row along the longitudinal axis, and
    wherein the support is disposed between the connector receptacle and the header and at least partially surrounds the connector ring blocks and the insulating rings of the connector receptacle, the support exerting an axial compressive force to retain the connector receptacle under axial compression along the longitudinal axis.

2. The implantable pulse generator of claim 1, wherein the support at least partially surrounds the connector receptacle as a result of the support being over-molded about the connector receptacle.

3. The implantable pulse generator of claim 1, wherein the support retains the connector receptacle under the axial compression by a press-fit.

4. The implantable pulse generator of claim 1, wherein the support includes a window positioned over a first connector ring block of the connector ring blocks, and a conductor ribbon extends from a feedthru of the housing and through the window to electrically couple the conductor ribbon with the first connector ring block.

5. The implantable pulse generator of claim 4, wherein the support further includes a circumferential rib of a sidewall of the support, the circumferential rib being immediately adjacent the window and fully covering a a first insulating ring of the insulating rings, the first insulating ring underlying the circumferential rib of the sidewall.

6. The implantable pulse generator of claim 5, wherein the circumferential rib extends across the first insulating ring in an axial direction, and along the first insulating ring in a circumferential direction to isolate the first insulating ring from the header.

7. The implantable pulse generator of claim 1, wherein the support defines a recess configured to be mated with a tip block that is discrete from the connector receptacle or a ring block that is discrete from the connector receptacle.

8. The implantable pulse generator of claim 1, wherein the support defines a slot configured to receive a ribbon conductor of the connector assembly.

9. The implantable pulse generator of claim 1, further comprising a suture opening in the header connector assembly, wherein the suture opening is defined by the header.

10. The implantable pulse generator of claim 1, wherein the support includes a sidewall that defines windows spaced apart along the longitudinal axis, and the support surrounds an entirety of the connector receptacle except for portions of the connector ring blocks that are exposed through the windows defined through the sidewall.

11. The implantable pulse generator of claim 1, wherein the support extends beyond the proximal and distal ends of the connector receptacle and exerts the axial compressive force on the proximal and distal ends.

* * * * *